(12) United States Patent
Moore

(10) Patent No.: US 9,615,573 B1
(45) Date of Patent: Apr. 11, 2017

(54) PRODUCT AND METHOD FOR PROVIDING ANTI-MICROBIAL DELIVERY

(71) Applicant: Rose M. Moore, Somerset, NJ (US)

(72) Inventor: Rose M. Moore, Somerset, NJ (US)

(*) Notice: Subject to any disclaimer, the term of this patent is extended or adjusted under 35 U.S.C. 154(b) by 0 days.

(21) Appl. No.: 14/121,425

(22) Filed: Sep. 4, 2014

(51) Int. Cl.
 *A61K 36/00* (2006.01)
 *A01N 25/08* (2006.01)

(52) U.S. Cl.
 CPC .......... *A01N 25/08* (2013.01); *A01N 2300/00* (2013.01); *A61K 2236/00* (2013.01)

(58) Field of Classification Search
 None
 See application file for complete search history.

(56) References Cited

U.S. PATENT DOCUMENTS

| | | | |
|---|---|---|---|
| 2,527,955 A | 10/1950 | Pagel | |
| 4,008,351 A | 2/1977 | Inoue et al. | |
| 4,832,942 A | 5/1989 | Crace | |
| 4,856,140 A | 8/1989 | Visco et al. | |
| 4,953,703 A | 9/1990 | Virginio | |
| 5,054,063 A | 10/1991 | Lo et al. | |
| 5,076,265 A | 12/1991 | Wokalek | |
| 5,136,640 A | 8/1992 | Kim | |
| 5,579,769 A * | 12/1996 | Yoshida | A61K 49/226 528/60 |
| 5,786,282 A | 7/1998 | Carter et al. | |
| 5,882,667 A * | 3/1999 | Jones | A01N 25/34 424/405 |
| 5,987,645 A | 11/1999 | Teaster | |
| 6,211,450 B1 | 4/2001 | Ishida | |
| 6,215,871 B1 | 4/2001 | Conolly et al. | |
| 6,358,519 B1 | 3/2002 | Waterman | |
| 6,645,435 B2 | 11/2003 | Dawson et al. | |
| 6,821,325 B1 | 11/2004 | Williams et al. | |
| 6,869,085 B2 | 3/2005 | Pettigrew | |
| 7,128,929 B1 | 10/2006 | Scherr | |
| 7,229,689 B2 | 6/2007 | Qin et al. | |
| 7,290,654 B2 | 11/2007 | Hodges | |
| 7,420,024 B2 | 9/2008 | Chu et al. | |
| 7,669,736 B2 | 3/2010 | Harper | |
| 7,690,050 B2 | 4/2010 | Stockhamer | |
| 7,722,589 B2 | 5/2010 | Fitts, Jr. et al. | |
| 7,750,201 B2 | 7/2010 | Patel et al. | |
| 7,757,351 B2 | 7/2010 | Davis, Jr. | |
| 7,862,877 B2 | 1/2011 | Balzano | |
| 7,960,010 B2 | 6/2011 | Kliesch et al. | |
| 7,981,946 B2 | 7/2011 | Krishnan | |
| 8,048,517 B2 | 11/2011 | Kimball et al. | |
| 8,080,301 B2 | 12/2011 | Goodwin et al. | |
| 2005/0251082 A1 * | 11/2005 | Del Bono | A61F 13/36 602/41 |
| 2006/0210062 A1 | 9/2006 | DeMichele et al. | |
| 2008/0057811 A1 | 3/2008 | Yahiaoui et al. | |
| 2010/0281781 A1 | 11/2010 | Badgley et al. | |
| 2011/0111000 A1 | 5/2011 | Russell et al. | |
| 2011/0206817 A1 | 8/2011 | Arnold et al. | |
| 2011/0223227 A1 | 9/2011 | Badgley et al. | |
| 2011/0287074 A1 | 11/2011 | Jin et al. | |
| 2012/0017802 A1 | 1/2012 | McDaniel | |

FOREIGN PATENT DOCUMENTS

| | | | | |
|---|---|---|---|---|
| EP | 944291 A1 | 9/1999 | | |
| GB | 2439525 A * | 1/2008 | .......... | A61F 13/104 |
| JP | 11062331 A | 3/1999 | | |
| WO | 9011015 A1 | 10/1990 | | |
| WO | 2011065861 A1 | 6/2011 | | |
| WO | 2011163327 A2 | 12/2011 | | |

OTHER PUBLICATIONS

Rivero et al, An antibacterial submicron fiber mat with in situ synthesized silver nanoparticles. Journal of Applied Polymer Science (2012), 126(4), 1228-1235.*

Nissen, Antimicrobial efficacy of a silver layer on hydrogel Lenses. Der Ophthalmologe : Zeitschrift der Deutschen Ophthalmologischen Gesellschaft, (Sep. 2000) vol. 97, No. 9, pp. 640-643.*

Quang et al, Preparation of amino functionalized silica micro beads by dry method for supporting silver nanoparticles with antibacterial properties. Colloids and Surfaces, A: Physicochemical and Engineering Aspects (2011), 389(1-3), 118-126.*

Zhou, A photopolymerized antimicrobial hydrogel coating derived from epsilon-poly-L-lysine. Biomaterials, (Apr. 2011) vol. 32, No. 11, pp. 2704-2712.*

* cited by examiner

*Primary Examiner* — Qiuwen Mi
(74) *Attorney, Agent, or Firm* — Tini Thomas, Esq., LLC

(57) ABSTRACT

A product and method for delivering antibacterial protections to a person's body to prevent the transmission of germs from contact surfaces wherein the contact surface is sanitized intermittently, on an as-needed-basis when touch is applied on the biodegradable organic hydrogel solid of said product.

3 Claims, 8 Drawing Sheets

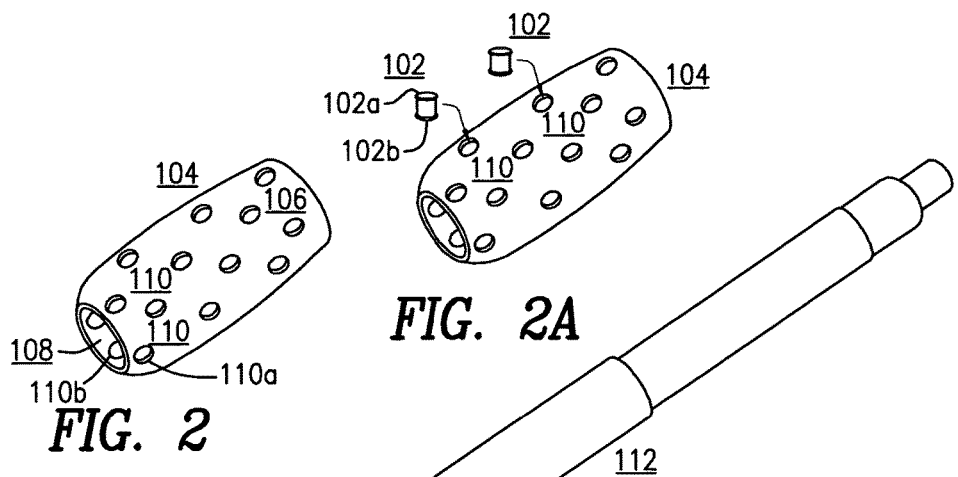
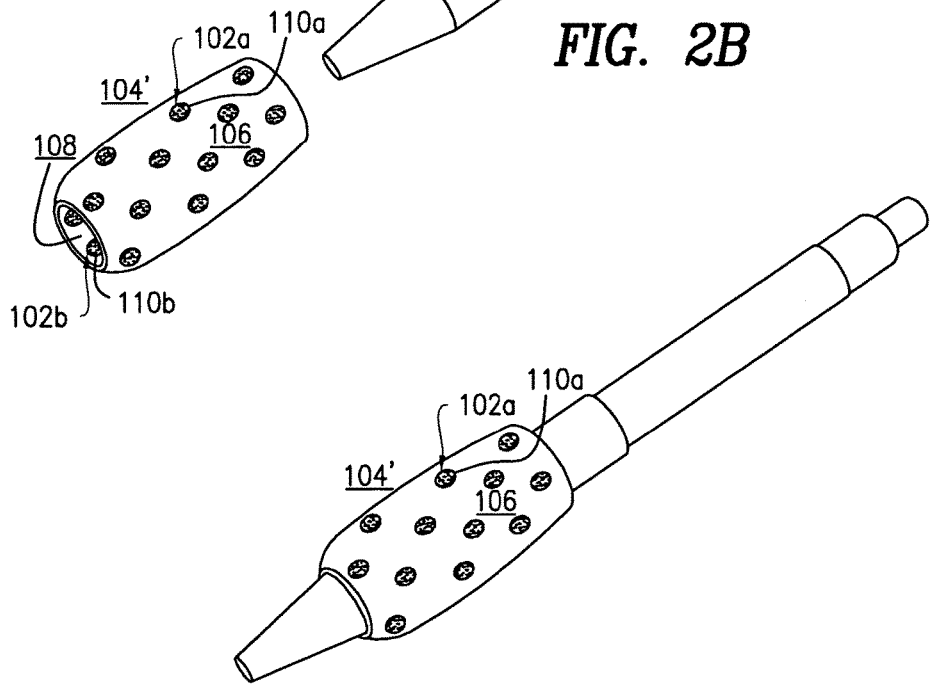
FIG. 2
FIG. 2A
FIG. 2B
FIG. 2C

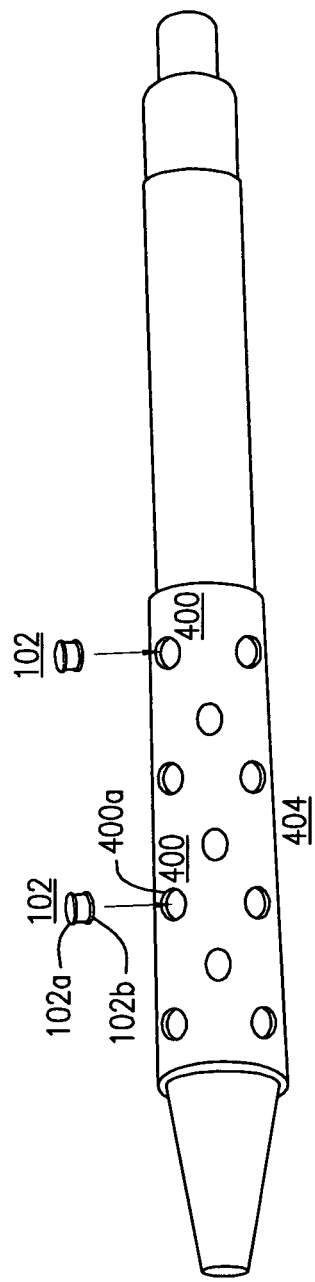
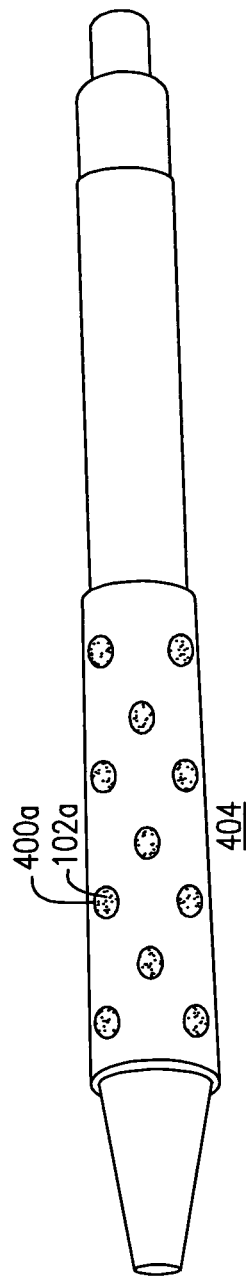
FIG. 4A
FIG. 4B

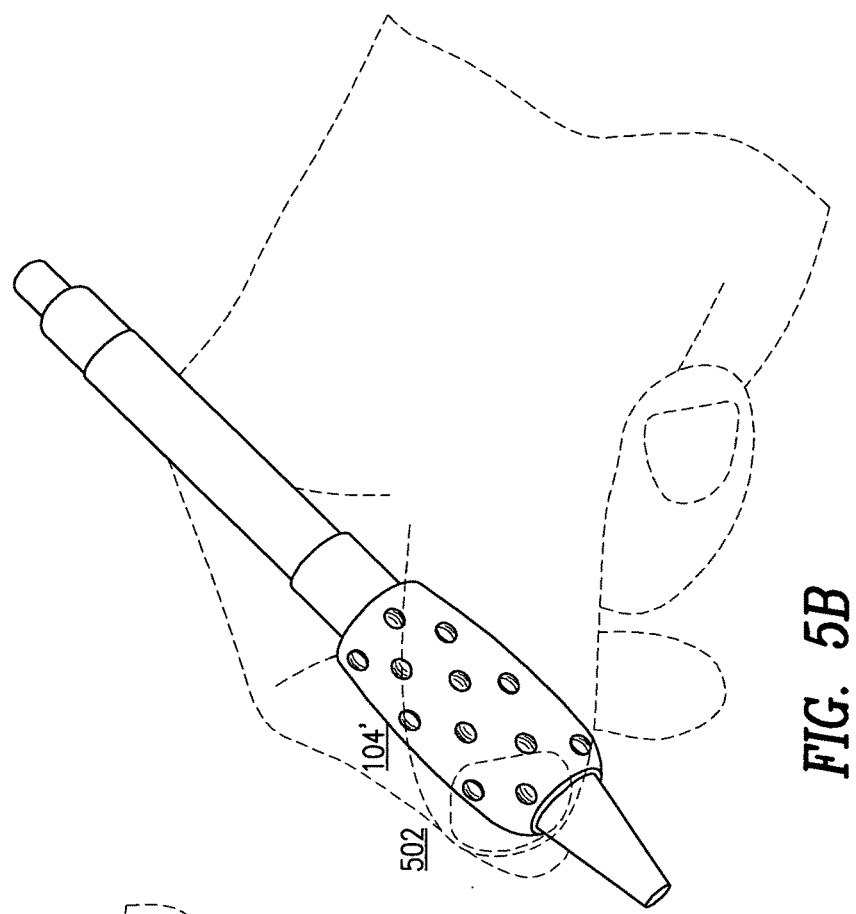
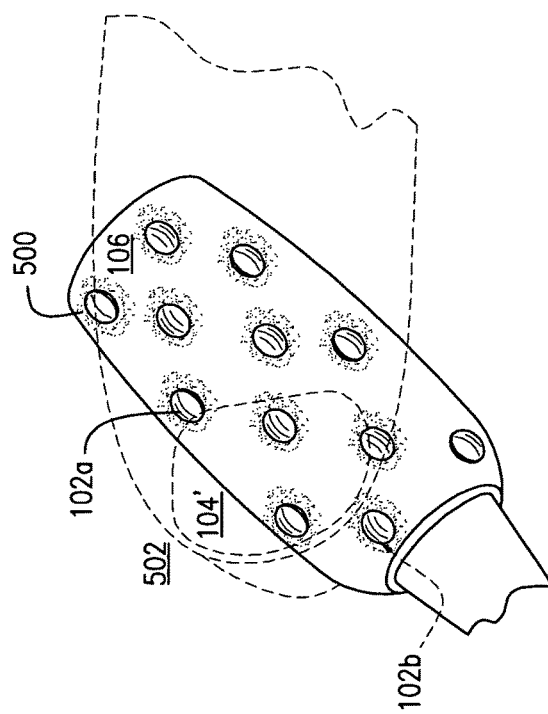
FIG. 5A
FIG. 5B

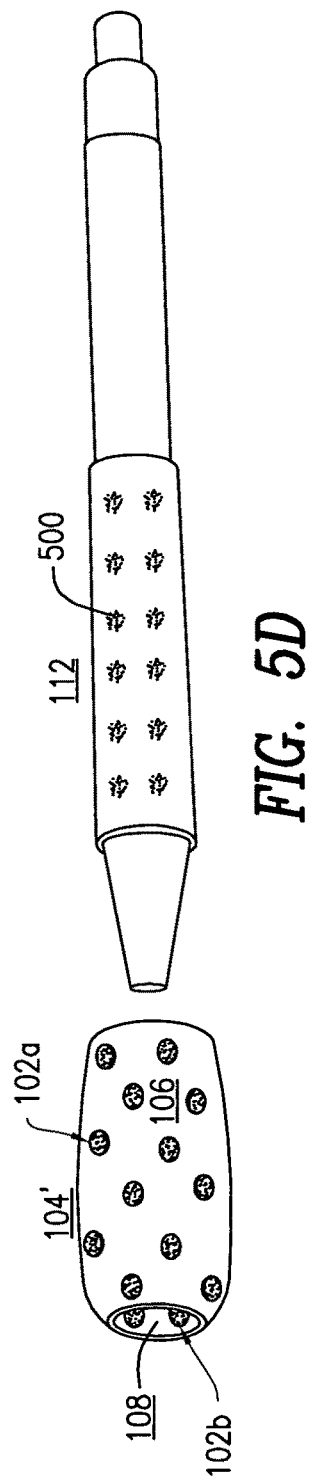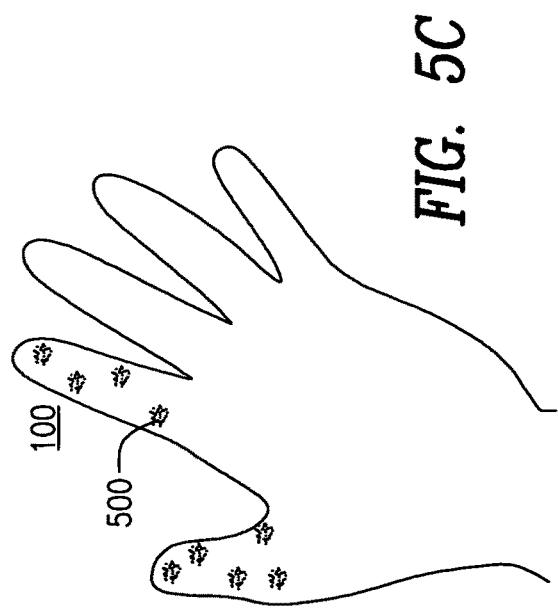
FIG. 5D
FIG. 5C

PRODUCT AND METHOD FOR PROVIDING ANTI-MICROBIAL DELIVERY

FIELD OF THE INVENTION

The present invention relates to a form of infection and disease control among high traffic contact surfaces. More particularly, the present invention relates to a product and method for delivering antibacterial protections to individuals by preventing the transmission of germs from high traffic contact surfaces, such as pens, car mats, rugs, doorbells, elevator push buttons or door knobs, etc., thus providing deterrence to the growth of bacteria, molds and fungi.

BACKGROUND OF THE INVENTION

The skin is the largest organ for humans. The skin can be susceptible to infection due to germs and bacteria. Infection occurs when direct skin contact is made between people and shared contact surfaces. Direct skin contact with people and shared contact surfaces can lead to the spread of germs that cause disease. To prevent the spread of disease, people are advised to regularly clean their hands. It is known that germs, viruses and similar potentially health-threatening bacteria are found on a variety of contact surfaces. Examples of some shared contact or high traffic contact surfaces, include office pens, at the local DMV (Division of Motor Vehicles) or doctor's offices, bathroom doors, elevator buttons, doorbells, door handles, car mats and rugs.

While various hand and skin sanitizers, germ-free guards, and gentle-acting skin-disinfectants are in the prior art and in the market, most are commonly chemical based and liquid in nature. The current line of sanitation products disclosed in the prior art and out on the market today have many disadvantages, including liquid leakage; a wet or moist initial sensation on the skin and then dryness of the skin; waste and sloppy delivery, especially where a product has a continuous delivery system which results in oversaturation of the device.

The current product line of sanitizers produces limited success, in view of the fact that the overwhelming use of chemical ingredients in sanitation products causes skin dryness, rashes and irritations. The skin's natural barrier, as well as, naturally retained moisture, and oils are destroyed and compromised when sanitation products are applied. Also with the increased awareness of the health and wellness movement, with the current generation desiring more "green" or natural organic products to be used to minimize both use and production of harmful chemicals, the current line of sanitation products, disclosed in the prior art and in the market today, do not meet the needs and desires of many of the current consumers.

There is a need for an environmentally safe, more organic and natural, solid sanitizer that provides anti-microbial delivery with the minimum amount of chemical ingredients, while retaining moisture and enhancing the skin's natural barrier with organic oils. The prior art does not provide the benefit of a solid sanitizers, predominately organic, and consisting mostly of natural ingredients, and minimal chemicals, that can be used in multiple applications on a variety of contact surfaces to prevent the spread of disease, germs and viruses.

There is a necessity for an affordable, efficient, and versatile product, which is solid, predominately organic, consisting mostly of natural ingredients, to sanitize and destroy the growth of disease-causing microorganisms on contact surfaces while also protecting a person's body. Additionally a method for antibacterial delivery to a person's body to protect them from germs using a novel organic solid is also desirable.

SUMMARY OF THE INVENTION

The invention disclosed herein relates to a product and method for delivering antibacterial protections to a person's body to prevent the transmission of germs from common contact surfaces such as a pen, car mat or rug, doorbell, elevator push buttons, door knob, etc., where both the contact surface and skin are sanitized intermittently, on an as-needed-basis when touch is applied on the biodegradable organic hydrogel solid of said product. The product may include beads, rods or any shape of disinfecting, sterilizing, sanitizing, hydrogel solids, capable of destroying or inhibiting the growth of disease-causing microorganisms, secured onto or covering the contact surface where germs could potentially grow.

This invention relates to a product with at least one solid self-contained gelled reservoir comprising of natural or organic biocides and germicides which distributes by touch release on an as-needed-basis. The solid self-contained gelled reservoir is configured to release an anti-microbial application to both, the skin and a high traffic surface when compressed. The invention is pressure sensitive. The pressure of the skin on the product causes a beneficial microbial application to be released from the product onto the pressure point of the skin and onto the high traffic surface in a solid form.

This product allows for an anti-microbial delivery with at least one solid self-contained gelled reservoir comprising of biocides, germicides, natural or organic, safe for the body (considered "GRAS" classification—generally regarded as safe by EPA), which distributes the solid composition by touch release on an as-needed-basis for protection of human hands and skin against germ hoarding surfaces, while sanitizing high traffic surfaces. Once the product is touched, for example by the skin gliding over it, a beneficial microbial application to kill germs is released directly onto the skin in solid form (in the same way that a solid stick antiperspirant is applied), as well as released onto the high traffic surface where the product is located over. Pressure on the product releases the anti-microbial substance. This product uses no plastic, liquids, vapors or films and is unique from the prior art in the field. This product prevents excessive leakage and waste associated with continuous sanitization.

Furthermore, the biodegradable solid organic hydrogel used will wear down with usage and disintegrate. The product may be rich in phenols, prepared with essential oils and natural products, including, tree oil, black seed oil, menthol, *laurus nobilis*, zinc, silver, honey, apple cider vinegar, witch hazel, thymes, eugenol-clove, guaiacol isolated from *Ocimum gratissimum*, and neem oil. The combination of essential oils and natural products is unique, natural and organic which allows for effective application without destroying the skin's delicate barrier. A certain number of chemicals may be used including, calcium hydroxide, iodine, peroxide, ethanol, chlorhexidine gluconate, and oxygen bleach. In one embodiment, the product may include 20% to 30% of essential oils and organic products and 10% to 20% of chemicals. Thus the product is predominately organic.

The product disclosed herein has multiple applications for the protection of skin against germ hoarding contact surfaces at homes, offices, hospitals, buildings, protecting the contact surface it is placed on, and delivering the antibacterial application onto the point of contact of an individual's skins of any person who uses the product until the product has been used up and disintegrates.

The product disclosed herein satisfies the long felt needs for effective sanitizer by adding the benefits of a solid, predominately organic antimicrobial delivery system, and solves the limitations of the prior art in a new and novel manner.

The current invention is versatile and can be embedded in or affixed on various contact surfaces. It is designed to facilitate applications that prior art fails to address. Moreover, because this invention is a solid product no leakage or oversaturation will occur when the antimicrobial application is delivered. These are clear advantages over the prior art which uses liquid sanitizing agents. Additionally, the current invention is made of mostly organic ingredients which allows for greater retention of moisture and enhances the individual user's skin, thus preventing dryness of the skin and the spread of disease, germs and viruses.

One advantage of the present invention is the fact that there would be decreased microbial capacity available for the spread of disease, germs and viruses to all who use this invention. This would lead to the reduction of infectious disease and the transfer of germs to the public at large. The current invention would also give its users peace of mind, in that they would know that this product prevents the multiplication of infection causing microbes. In addition, the protection against germs and bacteria provided by the present invention lasts the life-time of the product.

Another advantage of the present invention is the extended shelf life of the product. This invention has high product stability for several months and will degrade over time. The current invention is unlike other products on the market which break down or have shelf life degradation due to exposure to environmental elements, such as light, heat, or moisture.

Still another advantage of the present invention is that it has the potential to decrease health care costs. If infections decrease among the general public, there will be fewer days spent in the hospital, at clinics and away from work. In addition, the constant uprising of resistant microbes would be on the decline, for there would be fewer places for them to proliferate, and thus, fewer areas for such microbes to infect the general population.

These and other aspects of the present invention will become apparent to those of ordinary skill in the art by reference to the following description and to the appended drawings.

BRIEF DESCRIPTION OF THE DRAWINGS

FIGS. 2, 2A, 2B, and 2C show an anti-microbial delivery product in accordance with another embodiment of the present invention with a removable delivery means.

FIG. 4A and FIG. 4B show an anti-microbial delivery product in accordance with another embodiment of the present invention.

FIGS. 5A, 5B, 5C and 5D shows an anti-microbial delivery product in use in accordance with one embodiment of the present invention, wherein FIGS. 5C and 5D depict the dual distribution property of anti-microbial delivery on both the pressure applier and the object's contact surface.

DETAILED DESCRIPTION OF PREFERRED EMBODIMENTS

Figure 1:
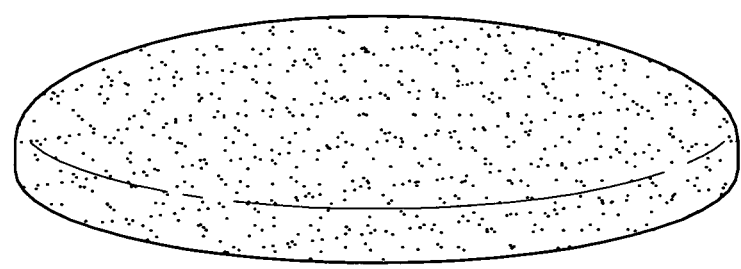
FIG. 1 shows a longitudinal frontal view of an anti-microbial delivery product in accordance with an embodiment of the present invention.

FIG. 1 shows a longitudinal frontal view of an anti-microbial delivery product in accordance with an embodiment of the present invention. The product may be a biodegradable solid organic hydrogel which provides anti-microbial delivery to a person's body to prevent the transmission of germs from a contact surface through touch release on an as needed basis, said product comprising: tree oil, black seed oil, menthol, *laurus nobilis*, zinc, silver, honey, apple cider vinegar, witch hazel, thymes, eugenol-clove, guaiacol isolated from *Ocimum gratissimum*, neem oil, calcium hydroxide, iodine, peroxide, ethanol, chlorhexidine gluconate, and oxygen bleach. The product is clear. It has a flexible, rubber like consistency. Due to its adhering nature, it can attach directly to any object without an adhesive. Color can be added through color additives or other known ingredients and/or methods apparent to those of ordinary skill in the art. As such, the product is versatile in color schemes that it offers to its users. Moreover, the versatility in color of the product allows it to blend in with the material that it is covering so that the product is not visibly detected. Additionally the shape of the product is not limited.

The product, a self-contained reservoir is a simple agar; gelatin material formation derived from a mixture prepared wherein the material properties are that of a hydrogel like structure. The product is prepared by first, combining the solute material: cellulose, glucose, and silicone polymers. Second, adding water that has been treated with chlorine (common bleach) (1-4 ppm) and allowed to sit one hour before use. Third, the treated water is added to the mixture and the placed in a thermal centrifuge at semi high temperature and semi high speed settings for cross linking to occur. Fourth, this is accomplished as various premeasured additives at different percentages (depending on application) are infused; such as botanicals: herbal extracts, oils, caffeine, borax, ethanol, (for example); and other agents all consisting of antibacterial properties. Other agents may include tree oil, black seed oil, menthol, *laurus nobilis*, zinc, silver, honey, apple cider vinegar, witch hazel, thymes, eugenol-clove, guaiacol isolated from *Ocimum gratissimum*, and neem oil. A certain number of chemicals may be used including, calcium hydroxide, iodine, peroxide, ethanol, chlorhexidine gluconate, and oxygen bleach. The biodegradable organic hydrogel solid product can be formed by any combination of the following, tree oil, black seed oil, menthol, *laurus nobilis*, zinc, silver, honey, apple cider vinegar, witch hazel, thymes, eugenol-clove, guaiacol isolated from *Ocimum gratissimum*, neem oil, calcium hydroxide, iodine, peroxide, ethanol, chlorhexidine gluconate, and oxygen bleach. Not all ingredients may be used at one time. In one embodiment, the product may include 20% to 30% of essential oils and organic products and 10% to 20% of chemicals. Fifth, when the mixture reaches the viscosity and homogenous solution tailored for the application intended then it is placed in containers to form the appropriate design, form, or structure molding a body for a particular application. Finally, the solution cools to a solid form. It is then cut to form and ready for application. The mixtures are either hydrophilic or hydrocolloidal in character or reversed functional properties agar mixtures, depending of its use in application.

In another embodiment of this invention, there is also a pouring while in liquid form into various application scaffolds and housing, wherein the solution is poured into a hollowed area or housing to become part of structure itself in application and allowed to solidify (cool) forming a particular shape, thus becoming one with or fused with intended structure.

Figure 1A:
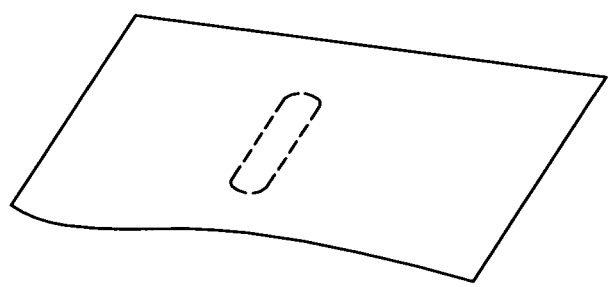
FIG. 1A shows top view of another embodiment of the product, wherein a strip 100 of the product is cut out.
Figure 1A:
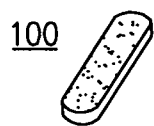

FIG. 1A shows top view of another embodiment of the product, wherein a strip 100 of the product is cut out. The strip 100 may be wrapped around an object or lay over any surface area.

Figure 1B:
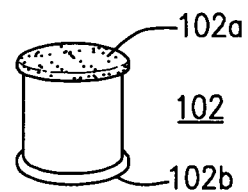
FIG. 1B shows a side frontal view of another embodiment of the product, wherein the product is cut or punched out to form the cylindrical rod 102 or cylindrical bead with two cylindrical ends, the top cylindrical end 102a, and the bottom cylindrical end 102b.

FIG. 1B shows a side frontal view of another embodiment of the product, wherein the product is cut or punched out to form the cylindrical rod 102 or cylindrical bead with two cylindrical ends, the top cylindrical end 102a, and the bottom cylindrical end 102b. The cylindrical bean rod 102 may be inserted into a delivery system.

The product can be cut into strips 100 to adhere to an object directly, or into cylindrical beads 102 that are embedded into an outer cover wherein the outer cover has holes so the beads touch the human skin and the contact surface of the object. The shape can be cut to meet the needs of the surface area to be covered and/or to the desired comfort or need of the users.

Thus, it should be appreciated that the advantages of this invention are not limited to requiring that the product have any particular size and/or shape.

FIG. 2 shows an outer and partial inner view of a removable delivery means 104 for an anti-microbial delivery product. The removable delivery means 104 is a covering for the high traffic surface area. The removable delivery means has an outer part 106 and an inner part 108. The removable delivery means has holes 110. The holes have a top 110a located on the outer part 106 of the removable delivery means and a bottom 110b located in the inner part 108 of the removable delivery means.

FIG. 2A shows an outer and partial inner view of a removable delivery means 104 for an anti-microbial delivery product wherein the product can be held in the removable delivery means 104. The product shaped as cylindrical rods 102 is inserted into the holes 110 of the removable delivery means with the bottom cylindrical end 102b entering the holes 110 first and the top cylindrical end 102a entering the holes 110 last.

FIG. 2B shows an outer and partial inner view of a filled removable delivery means 104' for an anti-microbial delivery product designed to fit on and around the contact area of the high traffic surface area 112, which in this figure is a writing instrument, a pen. The removable delivery means in this figure is filled 104' throughout with product. The top cylindrical end 102a of the cylindrical rod product is sticking out of the outer part 106 top rim or top of the hole 110a, and the bottom cylindrical end 102b of the cylindrical rod product is sticking out of the inner part 108 bottom of the hole 110b. The top of the hole 110a face away from the high traffic surface area. The bottom rim or bottom of the hole 110b in the inner layer 108 of the removable delivery means is also filled to with product. The inner layer 108 of the removable delivery means faces toward the high traffic surface area with the bottom of the hole 110b filled with product.

FIG. 2C shows the top longitudinal outer view of a filled removable delivery means 104' for an anti-microbial delivery product fit on and around the contact area of the high traffic surface area 112 of FIG. 2B, such that the contact area of the high traffic surface area 112 of FIG. 2B is completely covered. The top cylindrical end 102a of the cylindrical rod product is sticking out of the top of the hole 110a on the outer part 106 of the removable delivery means.

The removable delivery means 104 can be a sleeve made of any material that permits wrapping around the contact area of the high traffic surface area 112 which is a pen's gripping area, including but not limited to sponge, foam, cotton, neoprene, plastic, vinyl, rubber, or any other known material apparent to those of ordinary skill in the art. Once the product 102 disintegrates, removable delivery means 104 sleeve can be easily removed and a new sleeve filled with product replaced onto the object's high traffic surface area 112. The holes 110 on the removable delivery means 104 sleeve are cut out hollow areas where the product 102 can be inserted. The anti-microbial delivery product is encased in the removable sleeve with its cylindrical rods 102 body fitting in the holes 110 and the cylindrical rod ends 102a, 102b protruding from the respective ends of the holes 110a, 110b on both side of the sleeve, the outer part 106, and inner part 108.

Thus the product in the encased sleeve of the filled removable delivery means 104' is ready for use and protruding from the cylindrical rod ends 102a available to disinfect and sanitize the human hands that come into contact with the outer part 106 of the sleeve.

Figure 3:
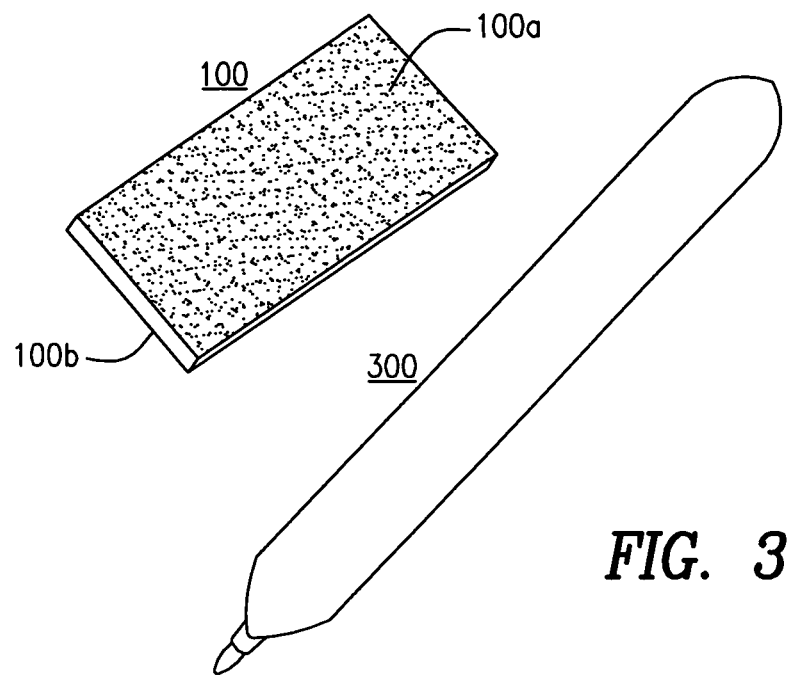
FIG. 3 and FIG. 3A show an anti-microbial delivery product in accordance with another embodiment of the present invention.

FIG. 3 shows the top longitudinal outer view of a rectangular strip 100 of the product and a high traffic surface area 300, which in this depiction is a writing instrument, a pen. The rectangular strip 100 has two sides, the outer side 100a and the inner side 100b.

Figure 3A:
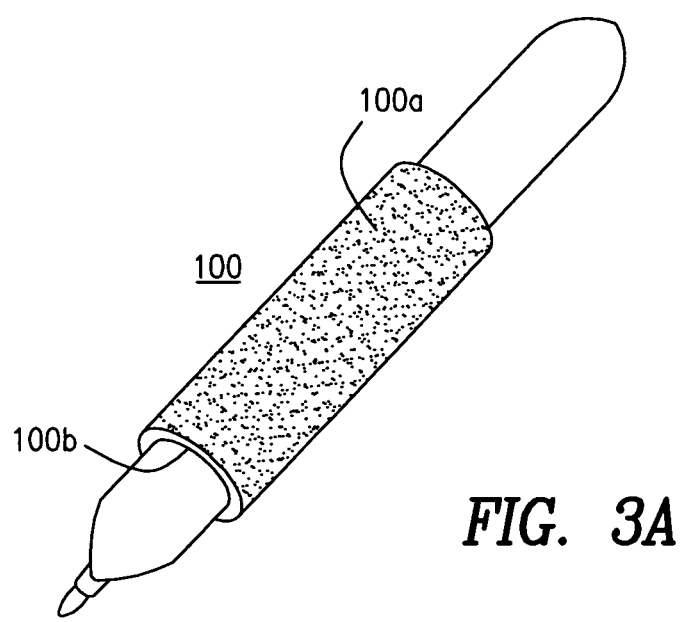

FIG. 3A shows the top longitudinal outer view of a rectangular strip 100 of the product where the inner side 100b wraps around the high traffic surface area 300 of FIG. 3 such that the contact area of the high traffic surface area 300 of FIG. 3 is completely covered. The outer side 100a is visible.

FIG. 3A shows an anti-microbial delivery product shaped as a rectangular strip 100 affixed directly onto the high traffic surface area 300 or gripping areas of a pen. When human fingers grip rectangular strip 100, then the pressure of the human touch causes the rectangular strip 100 to release an anti-microbial substance. Once the product rectangular strip 100 disintegrates, it can be easily replaced by a new product strip applied on the object.

FIG. 4A shows the top longitudinal outer view of a high traffic surface area, in this depiction, a writing instrument, a pen, with cavities, space, or hollowed-out indentations 400 on the gripping area 404 of the casing of the pen. The hollowed-out indentations 400 has a top 400a. The product shaped as cylindrical rods 102 is inserted into the indentations 400 of the pen's casing gripping area 404 with the bottom cylindrical end 102b entering the indentations 400 first and the top cylindrical end 102a entering the indentations 400 last. The top of the hollowed-out indentations 400a will be in contact with the top cylindrical end 102a.

FIG. 4B shows the top longitudinal outer view of the high traffic surface area of a pen's gripping area 404 with the top cylindrical end 102*a* of the product in contact with the top of the hollowed-out indentations 400*a*, such that the hollowed-out indentations 400 of FIG. 4A are completely covered and the top cylindrical end 102*a* of the product is visible.

While preparing the product in this embodiment of the invention, the product may also while in liquid form be poured into the hollowed-out indentations or housing to become part of the structure 404 itself and allowed to solidify (cool) forming a particular shape, thus becoming one with or fused with intended structure.

FIG. 5A shows the pressure applier, a human hand, in contact with filled removable delivery means 104' on the high traffic surface area of the pen. The pressure applier's contact with the filled removable delivery means 104' causes an anti-microbial delivery clear film residue 500 to be released from both ends of the cylindrical rod 102*a*, 102*b*. The top cylindrical end 102*a* is visible and located on the outer part 106 of the filled removable delivery means, while the bottom cylindrical end 102*b* is in the inner part removable delivery means and not visible.

FIG. 5B shows the pressure applier's human hand holding the high traffic surface area of the pen at the filled removable delivery means 104' with minimal effort in between the thumb and index finger. The product which is encased in the removable delivery means is pressure sensitive and when minimal force, even the gliding of the skin of the human hand 502, is applied onto the product, it releases a clear film residue.

In FIG. 5C the hand is being sanitized by the anti-microbial delivery. FIG. 5C shows the anti-microbial delivery clear film residue 500 on the contact areas of the human hand 100, which in this depiction are the palm side of the thumb and index finger of the human hand which held the filled removable delivery means. It is understood that people may use their thumb, index and middle finger, or other members to hold a pen. This depiction is not intended to limit the contact area. Any contact area 100 that interacts with the product such that a pressure, even minimal, is applied onto the product will result in the anti-microbial delivery evidenced by the clear film residue 500.

FIG. 5D shows the anti-microbial delivery clear film residue 500 on the gripping area of the high traffic area 112 of the pen. FIG. 5D also shows the top longitudinal outer view of a filled removable delivery means 104' wherein the inner part 108 has the bottom cylindrical end 102*b* of the product which interacted with the high traffic surface area 112 of the pen, such that when the pressure applier, the human hand, exerted force however minimal onto the pen, the anti-microbial delivery took place with the release of the clear film residue 500 onto the high traffic surface area 112 of the pen. The top cylindrical end 102*a* of the product interacted with the pressure applier, the human hand, as explained in FIG. 5A.

FIGS. 5C and 5D shows the dual distribution property of the present invention, which delivers an anti-microbial delivery clear film residue 500 simultaneously onto the pressure applier 502, the hand in FIG. 5C and the high traffic surface area 112 of the pen.

Evidence of this anti-microbial release is that small amount of clear film residue 500 left on the contact area of the human skin 100 and on the pen's contact surface 112 directly underneath where the human skin pressure was applied. This two side distribution of anti-microbial delivery on both the contact area of the human skin 100 and the object's contact surface 112 is a novel and useful feature of this invention.

The touch which causes the pressure on the cylindrical rod ends (102*a*, 102*b*), referred to as the pressure applier, is not limited to only human touch, but can be mechanical or by any non-human pressure, apparent to those of ordinary skill in the art.

Thus, it should be appreciated that the advantages of this invention are not limited to requiring that the contact surface be a pen, the touch be human, or that that the product have any particular size and/or shape.

Figure 6A:
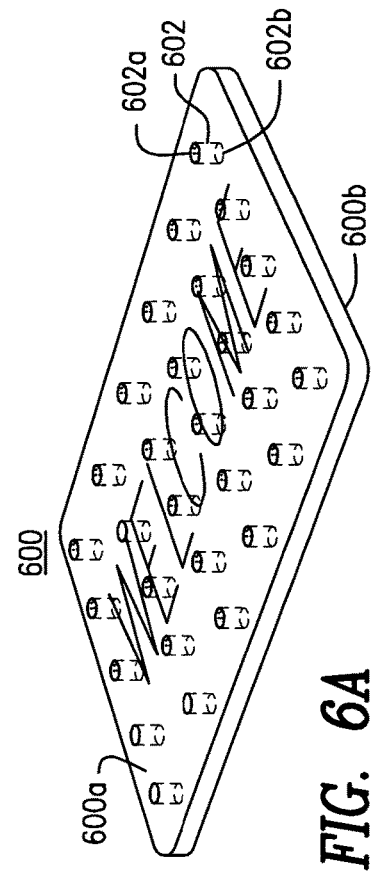
FIGS. 6A, 6B, 6C and 6D shows an anti-microbial delivery product in use in accordance with another embodiment of the present invention with dual distribution property of the residue released on the pressure applier and the high traffic surface area.

FIG. 6A shows the top and partial side view of filled removable delivery means, a surface area rug or mat, 600 which goes onto of high traffic surface area, a floor 604. The anti-microbial delivery product is cut into cylindrical rods 602 that are embedded throughout the welcome mat 600. The top cylindrical end 602*a* of the product on the front side of the mat 600*a*, while the bottom cylindrical end 602*b* of the product is on the bottom or the back side of the mat 600*b*. The mat depicted in this figure is a welcome mat.

Figure 6B:
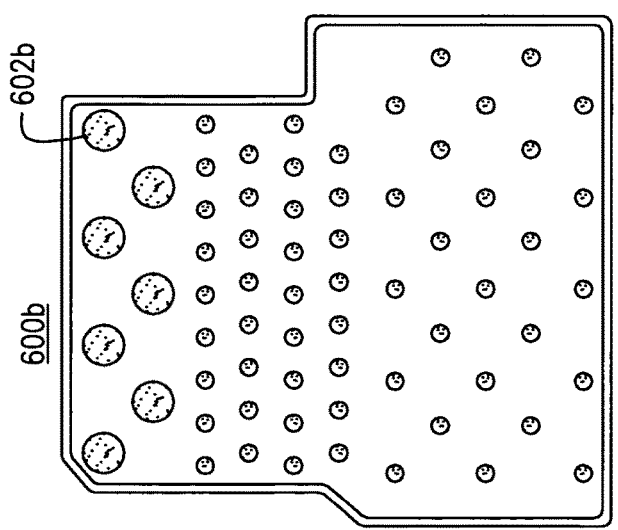

FIG. 6B shows the bottom or back side of the filled removable delivery means, a mat 600*b*. The bottom cylindrical end 602*b* of the product is shown here. The product is versatile in that the cylindrical end can be of any shape, size and dimension. The mat depicted in this figure is a car mat. The mat can take on any shape or dimension so long as it is able to be placed on the car's floor.

Figure 6C:
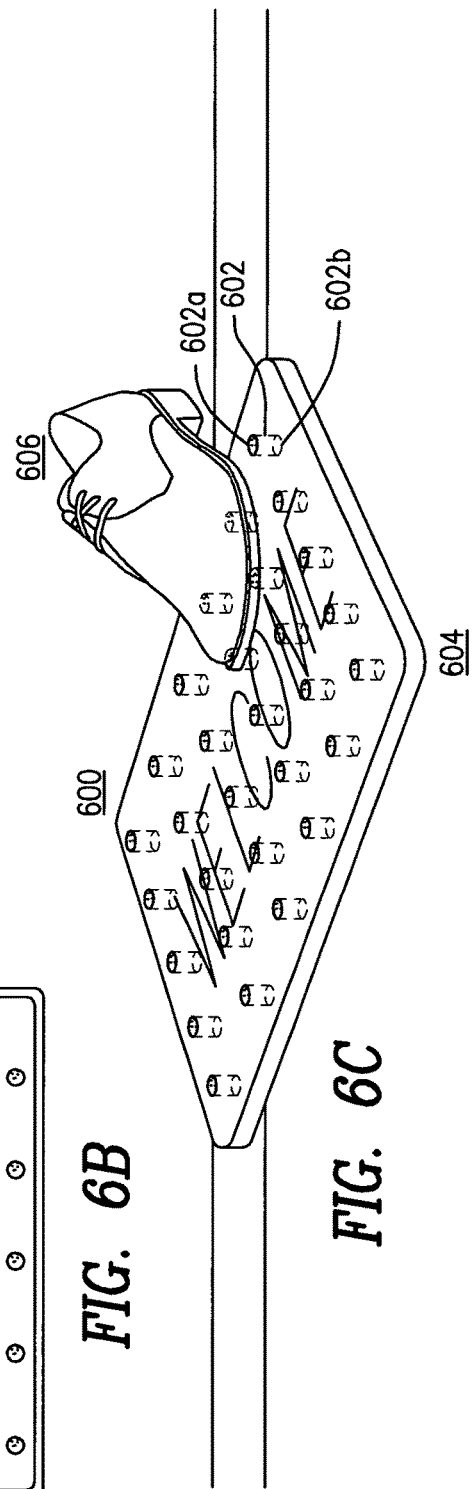

FIG. 6C shows a pressure applier, in this depiction, human footwear, a shoe 606, stepping onto the welcome mat 600, interacting with the cylindrical rods 602, exerting force on the cylindrical rods so that the top cylindrical end 602*a* connects with the bottom of the shoe 606 and bottom cylindrical end 602*b* connects with the floor 604.

Figure 6D:
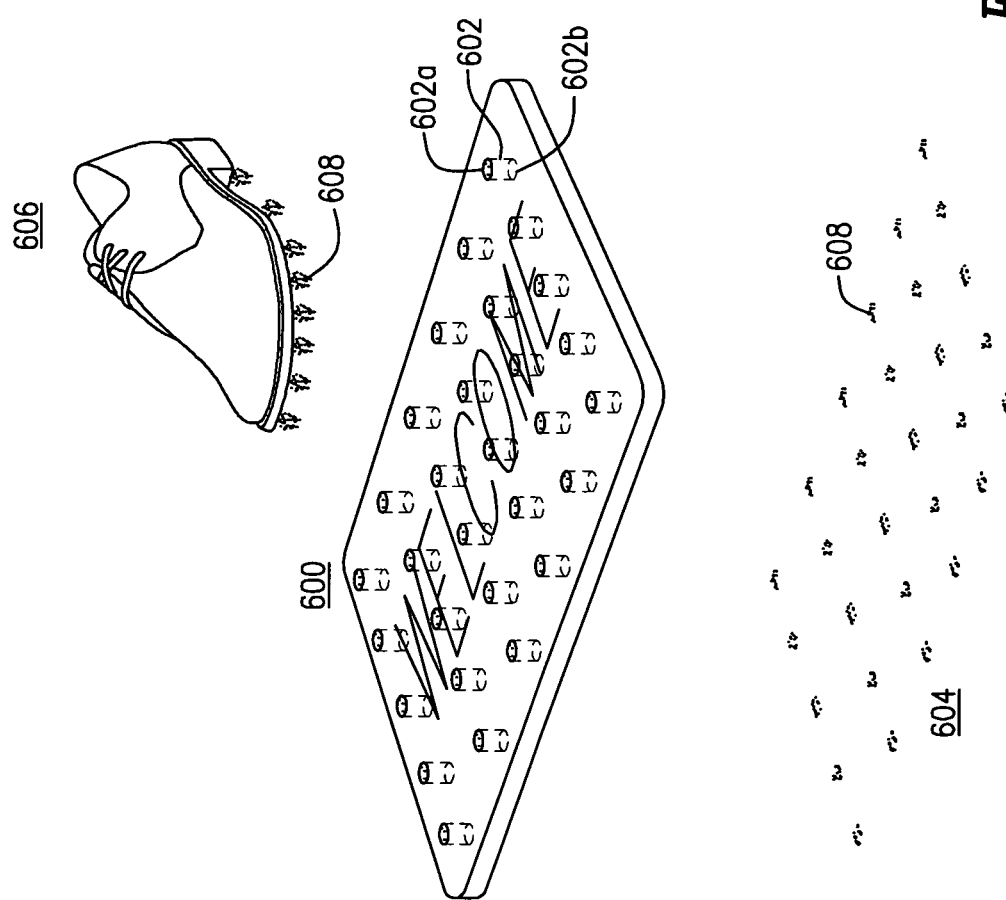

FIG. 6D shows a side frontal view of the shoe 606 lifted off the welcome mat 600 and the mat lifted off the floor 604, so that the anti-microbial delivery residue 608 is seen on the bottom of the shoe 606 and on the floor 604. FIG. 6D also shows the dual distribution property of the present invention, which delivers an anti-microbial delivery residue 608 simultaneously onto the pressure applier, the shoe 606, and the high traffic surface area, the floor 604. The cylindrical rods 602 release the residue 608 when from the top cylindrical end 602*a* which connected with the bottom of the shoe 606 and bottom cylindrical end 602*b* which connected with the floor 604 when pressure was exerted to the cylindrical rods 602.

In FIG. 6D shows an anti-microbial delivery product releasing a clear film residue simultaneously disinfecting and sanitizing both the pressure applier and the contact surface on an as needed basis. This two side distribution of anti-microbial delivery clear film residue 608 on both the pressure applier 606 and the object's contact surface 604 is a novel and useful feature of this invention.

The pressure applier 606 can be, but is not limited to, the pressure from a human foot, shoe, pet's paws, or mechanical pressure applied to the rug 600. The rug 600 can be made of any material that permits laying on a surface area, including but not limited to sponge, foam, cotton, neoprene, plastic, vinyl, rubber, or any other known material apparent to those of ordinary skill in the art.

The high contact surface areas depicted in the foregoing figures are pens and mats. The depictions are not meant to limit the invention. Other surface areas such as elevator buttons and door handles would also benefit from the current invention.

Although this present invention has been disclosed with reference to specific forms and embodiments, it will be evident that a great number of variations may be made without departing from the spirit and scope of the present invention. For example, steps may be reversed, equivalent elements may be substituted for those specifically disclosed and certain features of the present invention may be used independently of other features—all without departing from the present invention as defined in the appended claims.

What is claimed is:

1. A product for providing anti-microbial delivery to a person's body and to a contact surface area of an object to reduce the incidence of the transmission of germs, wherein the product comprises an anti-microbially effective amount of the following components:
   (i) tree oil,
   (ii) black seed oil,
   (iii) menthol,
   (iv) *laurus nobilis*,
   (v) zinc,
   (vi) silver,
   (vii) honey,
   (viii) apple cider vinegar
   (ix) witch hazel,
   (x) thymes,
   (xi) eugenol-clove,
   (xii) guaiacol isolated from *Ocimum gratissimum*,
   (xiii) neem oil,
   (xiv) calcium hydroxide,
   (xv) iodine,
   (xvi) peroxide,
   (xvii) ethanol,
   (xviii) chlorhexidine gluconate, and
   (xix) oxygen bleach,
   and wherein the product is a biodegradable organic hydrogel solid.

2. A product according to claim 1 wherein said object is pen.

3. A product according to claim 1 wherein said object is car mat.

* * * * *